United States Patent [19]

Marguerre et al.

[11] Patent Number: 6,007,979
[45] Date of Patent: Dec. 28, 1999

[54] METHOD FOR REDUCTION OF THE INFECTIOUSNESS OF POTENTIALLY INFECTIOUS MATERIAL

[75] Inventors: Wolfgang Marguerre, Helsingborg, Sweden; Horst Schwinn, Mainz; Lothar Biesert, Offenbach, both of Germany

[73] Assignee: Octapharma AG, Ziegelbrucke, Switzerland

[21] Appl. No.: 08/952,442

[22] PCT Filed: Apr. 4, 1996

[86] PCT No.: PCT/EP96/01488

§ 371 Date: Feb. 19, 1998

§ 102(e) Date: Feb. 19, 1998

[87] PCT Pub. No.: WO96/36369

PCT Pub. Date: Nov. 21, 1996

[30] Foreign Application Priority Data

May 20, 1995 [EP] European Pat. Off. ............ 95 107 710

[51] Int. Cl.⁶ ...................................................... A01N 1/02
[52] U.S. Cl. ........................... 435/2; 424/176.1; 424/529; 424/530; 424/531

[58] Field of Search ............................... 435/2; 424/176.1, 424/529–531

[56] References Cited

U.S. PATENT DOCUMENTS 4,789,545  12/1988  Woods et al. ............................ 424/101
5,648,472  7/1997  Gehringer et al. ...................... 530/412

*Primary Examiner*—Jeffrey Stucker
*Attorney, Agent, or Firm*—Jacobson, Price, Holman & Stern PLLC

[57] ABSTRACT

A method for reduction of the viral infectiousness of potentially infectious material, such as human or animal body fluids or fractions derived therefrom from which biologically active substances can be isolated, wherein the infectiousness is due to non-lipid-coated viruses characterized in that said potentially infectious material for the isolation of said biologically active substances is treated with a hydrophobic phase which is essentially insoluble in water and is capable of forming a two-phase system with said potentially infectious material, and said hydrophobic phase is separated from the potentially infectious material thus treated.

16 Claims, No Drawings

METHOD FOR REDUCTION OF THE INFECTIOUSNESS OF POTENTIALLY INFECTIOUS MATERIAL

This application is a nation stage filing of PCT/EP96/01488, filed Apr. 4, 1996, which claims priority of EPO 95 107 710.6, filed May 20, 1995.

The object of the present invention is a method for reduction of the viral infectiousness of potentially infectious material, such as human or animal body fluids or fractions derived therefrom from which biologically active substances can be isolated, wherein the infectiousness is due to non-lipid-coated viruses.

Potentially infectious materials, such as human or animal body fluids, are an important pool of biologically active and hence valuable substances. However, isolation of the biologically active substances from these sources is not unproblematic which has become apparent in the past especially in the case of HIV transmission by preparations recovered from blood plasma. Thus, an essential requirement for the administration of such preparations is their being virus-proof, i.e. no infectious particles must be transmitted with these preparations.

Viruses which are lipid-coated are effectively inactivated by treatment with non-ionic biocompatible solvents and detergents. Such methods are described in EP 0 131 740. Non-lipid-coated viruses are not adequately inactivated by such treatment. WO 94/17834 reports that an adequate inactivation of non-lipid-coated viruses, such as hepatitis A viruses, for instance, is achieved only by combined treatment of a solution by non-ionic detergents and heating thereof at 60 to 65° C. However, the heat treatment period being as long as more than 5 to 30 hours represents a drawback since the valuable biologically active substances are predominantly proteins, the complex structure of which is altered or even destroyed by such heat treatment. This involves reduction of the activity of the corresponding fractions. Thus, the known methods result in a reduction of the potential recovery of these products.

DE 40 21 542 A1 discloses a combined process for the preparation of non-infectious blood plasma. The plasma is treated with non-ionic tensides and prior to removal of the lipid layer are added biologically compatible lipids. Thereafter, the lipid phase is separated and the non-ionic tenside is removed by solid phase extraction on hydrophobic materials.

EP-A 0 239 859 is concerned with a method of removing lipid soluble process chemicals from biological materials containing the lipid soluble process chemicals. The method comprises bringing the biological materials containing the lipid soluble process chemicals into contact with an effective amount of a naturally occurring oil extracted from a plant or an animal or a synthetic compound of similar chemical structure. Agitating the resulted mixture, separating out an upper-phase and a lower-phase by the sedimentation and decanting the upper-phase. The method is particularly useful for producing physiologically acceptable plasma relatively virus free.

European patent application EP-A 0 525 502 discloses a process for manufacturing of virus inactivated immunoglobulin solutions for intravenous application. The immunoglobulin is treated with non-ionic tensides which are removed subsequently by solid phase extraction on hydrophobic materials.

European patent application EP-A 0 112 563 discloses a solvent treatment of plasma protein products. Plasma protein products are slurried in a dry state with an organic solvent to remove virus infectivity.

WO-A 83/04371 discloses a method of inactivating a lipid virus in a protein carrier selected from the group consisting of hepatitis B virus (HBV) and non-A, non-B hepatitis (NANBH) by contacting said virus for an extended period of time and ambient temperature with a halohydrocarbon treating agent preferably chloroform in an amount of 5% v/v to 50/50% v/v.

The problem underlying the invention is to provide a method by which a reduction of the infectiousness of non-lipid-coated viruses contained in potentially infectious or actually infectious materials can be achieved.

Surprisingly, it has been shown that infectiousness due to non-lipid-coated viruses in potentially infectious materials can be reduced by treatment of such materials with a hydrophobic phase capable of forming a two-phase system with said potentially infectious material and separation of the phases formed.

The method according to the invention for reduction of the viral infectiousness of potentially infectious material, such as human or animal body fluids or fractions derived therefrom from which biologically active substances can be isolated, wherein the infectiousness is due to non-lipid-coated viruses is characterized by the following measures. The potentially infectious material for the isolation of the biologically active substances is treated with a hydrophobic phase which is essentially insoluble in water and will form a two-phase system with said potentially infectious material. Thereafter, the hydrophobic phase is separated from the potentially infectious material thus treated.

In the following, by a potentially infectious material is also meant actually infectious material. In particular, this includes body fluids such as blood or blood plasma or processed blood or blood plasma, such as cryoprecipitate. In addition, however, this includes any fractions of such potentially infectious materials as well as cell lysates or similar natural sources.

The biologically active substances which can be isolated from the potentially infectious material are, in particular, proteins, such as factors of the blood-clotting cascade, such as factor VIII or vitamin K dependent factors, such as the C and S proteins, gamma-globulins, complementary factors, and serin protease inhibitors.

In particular, the hydrophobic phase capable of forming a two-phase system with the potentially infectious material which can be employed according to the invention is a non-polar organic liquid, such as a liquid which is an oil at room temperature, such as vegetable oil, or low-melting fats.

Not only is the method according to the invention compatible with existing methods for virus inactivation by means of non-ionic detergents and dialkyl or trialkyl phosphates, but it has proven a further advantage to complement the hydrophobic phase treatment of the potentially infectious material with a treatment with non-ionic detergents and dialkyl or trialkyl phosphates, especially tri-n-butyl phosphate (TNBP). This combined treatment can be performed simultaneously or sequentially.

The following derivatives may be mentioned as non-ionic detergents, which should be present in amounts of at least 0.1% by weight: bile salts, polyoxyethylene derivatives of fatty acids, partial esters of sorbitol anhydride, e.g. products traded under the designations of TWEEN 80, TWEEN 20 and POLYSORBAT 80, as well as non-ionic, oil-soluble surfactants, especially those known by the trade name of TRITON X-100 (ethoxylated alkylphenols). Also possible are zwitterionic reagents, for example, sulfobetains, such as N-dodecyl-N,N-dimethyl-2-ammonio-1-ethanesulfonate or derivatives thereof, or non-ionic detergents, such as octyl-β-D-glucopyranosides. The amount of detergents is preferred to be from 0.01% to 10%. Preferred treatments involve combinations of TNBP, TWEEN and TRITON, or sodium cholate/TNBP.

The treatment of the potentially infectious material with the hydrophobic phase is quasi substituted for the heat treatment step required in WO 94/17834 which, in combination with non-ionic detergents and alkyl phosphates, inactivates the non-lipid-coated viruses.

Possible non-lipid-coated viruses are in particular hepatitis A, coxsackie, polio and parvo viruses.

The method according to the invention is effective especially in the case that the hydrophobic phase is intimately mixed with the potentially infectious material. This can be achieved, for instance, by mechanical action, such as ultrasonic treatment, high-performance stirring, intense agitation etc.

After the two-phase system has been formed, the hydrophobic phase can be removed, in particular, by centrifugation or filtration. As the hydrophobic phase, there may be used, in particular, vegetable oils, such as soybean oil and/or castor oil. The oily phase can be removed by filtration through a hydrophobic filter. The degree of separation of the hydrophobic phase required primarily depends on the subsequent further processing. If the materials reduced in infectiousness by non-lipid-coated viruses are further purified, for example, by anion-exchange or affinity chromatography, then quantitative separation of the hydrophobic phase is not required. Therefore, it should be ensured that the infectious particles which may have been extracted into the hydrophobic phase are separated off. However, if a quantitative elimination of the hydrophobic phase is essential, said phase may be removed in a manner analogous to that described in DE 40 08 852. As separation procedures, the separation procedures common in biochemistry may be used, including electrophoresis.

The method according to the invention is excellently suitable for the isolation of biologically active substances, such as factors of the blood-clotting cascade, for example, factor VIII, vitamin K dependent clotting factors, etc.

The invention will be further illustrated by the following example.

EXAMPLE

To a potentially infectious blood plasma fraction, viruses are added which are not lipid-coated. The respective virus levels can be seen from the table. As non-coated viruses, coxsackie B6 and polio 1 were employed. Lipid-coated PRV virus is used as a control. Experiments have been performed with the non-lipid-coated viruses involving treatment with non-ionic detergents and TNBP (SD) or no such treatment ((−) in the SD column of the table). The sample is treated with oil.

To portions of about 20 ml each of a blood plasma fraction (e.g. containing factor VIII), coxsackie, polio, or pseudorabies viruses are added to the levels of infectious virus given in the table.

Subsequently, with intense stirring, 1. 0.2 ml of TWEEN 80 and 0.06 ml of TNBP are added to 19.74 ml of the fraction, or
2. 0.2 ml of TRITON X-100 and 0.2 ml of TNBP are added to 19.6 ml of the fraction.

1 ml each of castor oil is added to preparations 1 and 2 which are then intensely extracted at room temperature for one hour.

3. Another 20 ml of the virus-containing fraction is treated immediately with 1 ml of castor oil in the above manner without prior treatment with detergents (SD-).

Centrifugation is performed in each case for phase separation. For infectiousness control, samples of 1 ml each are repeatedly taken from the aqueous fraction.

| virus | SD | level before* | level after* | level reduction |
|---|---|---|---|---|
| PRV | − | 6.84 + 0.32 | 6.18 + 0.30 | 0.66 + 0.62 |
| coxsackie B6 | + | 6.96 + 0.32 | 2.79 + 0.17 | 4.17 + 0.49 |
|  | − | 6.78 + 0.23 | 3.56 + 0.32 | 3.22 + 0.55 |
| polio 1 | + | 7.02 + 0.38 | <2.73 + 0.12 | >4.29 + 0.50 |
|  | − | 6.90 + 0.32 | 4.16 + 0.28 | 2.74 + 0.60 |

*$\log_{10}$ TCID$_{50}$ per ml

We claim:

1. A method for the reduction of the viral infectiousness of potentially infectious material, from which biologically active substances can be isolated, wherein the infectiousness is due to non-lipid-coated viruses, comprising the steps of:
    treating said potentially infectious material with a hydrophobic phase that is essentially insoluble in water and is capable of forming a two-phase system with said potentially infectious material, and
    separating said hydrophobic phase from the potentially infectious material thus treated.

2. The method according to claim 1, wherein said potentially infectious material is human or animal body fluids or fractions derived therefrom.

3. The method according to claim 1, wherein said potentially infectious material is blood or blood plasma or processed blood or blood plasma.

4. The method according to claim 3, wherein said potentially infectious material is a cryoprecipitate.

5. The method according to claim 1, wherein said biologically active substances which can be isolated from said potentially infectious material are proteins.

6. The method according to claim 5, wherein said proteins are factors of the blood-clotting cascade.

7. The method according to claim 1, wherein said hydrophobic phase consists of non-polar organic liquids.

8. The method according to claim 7, wherein said non-polar organic liquids are oils or fats.

9. The method according to claim 1, wherein said potentially infectious material is further treated with non-ionic detergents and alkyl phosphates, or polyethers, simultaneously with or subsequent to said hydrophobic phase treatment for enhancing the effectivity of the reduction of infectiousness, thereof.

10. The method according to claim 9, wherein said alkyl phosphates comprise tri-n-butyl phosphate.

11. The method according to claim 9, wherein said polyethers comprise TRITON derivatives.

12. The method according to claim 1, wherein said hydrophobic phase is intimately mixed with said potentially infectious material, and the respective phases are separated following phase separation.

13. The method according to claim 1, wherein said material treated with said hydrophobic phase and reduced in infectiousness is further separated into fractions by a separation procedure.

14. The method according to claim 13, wherein said separation procedure is affinity chromatography, ion-exchange chromatography, electrophoresis, gel-permeation chromatography, or hydrophobic reverse phase chromatography.

15. The method according to claim 1 for the recovery of virus-inactivated biologically active substances.

16. The method according to claim 15, wherein said biologically active substances are factors of the blood-clotting cascade.

* * * * *